(12) United States Patent
Bennett (10) Patent No.: US 6,811,398 B2
(45) Date of Patent: Nov. 2, 2004

(54) HANDHELD RINSING DEVICE

(75) Inventor: Donald L. Bennett, 155 N. Michigan Ave., Chicago, IL (US) 60601

(73) Assignee: Donald L. Bennett, Chicago, IL (US)

( * ) Notice: Subject to any disclaimer, the term of this patent is extended or adjusted under 35 U.S.C. 154(b) by 162 days.

(21) Appl. No.: 10/121,416

(22) Filed: Apr. 11, 2002

(65) Prior Publication Data

US 2002/0150863 A1 Oct. 17, 2002

Related U.S. Application Data (60) Provisional application No. 60/283,985, filed on Apr. 16, 2001.

(51) Int. Cl.[7] .................................................. A61C 1/00
(52) U.S. Cl. .......................... 433/25; 433/49; 433/223; 433/229
(58) Field of Search ............................. 433/25, 49, 218, 433/219, 223, 229, 116; 451/89, 451, 452, 453, 454, 455, 456, 457; 134/901; 422/300

(56) References Cited

U.S. PATENT DOCUMENTS

| | | | |
|---|---|---|---|
| 709,181 A | * | 9/1902 | Sippel |
| 914,105 A | * | 3/1909 | Boland |
| 3,586,012 A | * | 6/1971 | Paule ........................ 134/93 |
| 4,475,370 A | * | 10/1984 | Stark et al. ..................... 72/53 |
| 5,381,912 A | * | 1/1995 | Walker et al. ............... 215/220 |
| 5,453,039 A | * | 9/1995 | Weintraub .................... 451/75 |
| 6,309,222 B1 | * | 10/2001 | Billingsley .................. 433/229 |

OTHER PUBLICATIONS

Text from Website http://eee.uci.edu/programs/gchem/filtration.pdf, 2 pages.
Text from Website http://www.xrefer/com/entry/639652, 1 page.

* cited by examiner

Primary Examiner—Cary E. O'Connor
(74) Attorney, Agent, or Firm—The Law Office of Randall T. Erickson, P.C.

(57) ABSTRACT

An apparatus for rinsing a dental restoration after etching, includes a base component having an open top end and a tubular extension terminating in an open bottom end. A shield component includes an open bottom end which is sized to fit onto the base component and has a tapered profile to an open top end. Within the base and shield components is carried a platform having one or more holes therethrough to allow fluid to pass from the shield component to the base component. In operation, a dental restoration is placed within the shield component onto the platform. Suction is drawn on the bottom open end of the base component and rinsing fluid is sprayed into the top open end of the shield component onto the dental restoration. Fluid which passes through the platform is suctioned through the bottom open end of the base component.

30 Claims, 7 Drawing Sheets

FIG. 7

HANDHELD RINSING DEVICE

This application claims the benefit of provisional application Ser. No. 60/283,985 filed Apr. 16, 2001.

TECHNICAL FIELD OF THE INVENTION

The invention is related to a vessel useful for treating an article with a chemical, a gel, liquid, spray or wash.

BACKGROUND OF THE INVENTION

In the field of dentistry, crowns or other restorations for repairing teeth must be precisely fabricated to match the contours of the defective tooth in order to restore proper shape, function and esthetics. In this regard, precise measuring of the tooth is undertaken by the dentist.

Restorations are fabricated of gold or other metal alloys, porcelain and composite resins. The invention is to be used in the preparation of porcelain restorations.

Porcelain restorations are currently fabricated in two ways. One method involves making an impression of the prepared tooth with impression material, then fabricating a refractory die. The die is utilized by a dental laboratory technician to fabricate the porcelain restoration. Porcelain powder is sculpted into the proper shape by the technician and then fired in a porcelain oven to create a solid porcelain mass.

The second method of fabrication utilizes computer-aided design and computer aided machining (CAD/CAM) of the dental restoration. In this method either a refractory die of the tooth or the tooth itself is scanned and digitized, the restoration is designed and milled out of a solid block of porcelain. This method can be used in a dental laboratory or in the dental office.

Before a porcelain restoration can be placed in a patient's mouth, the surface of the restoration must be prepared for bonding to the tooth structure. The porcelain which is to be bonded to tooth structure is first etched with a hydrofluoric acid gel, then rinsed with water, dried and then treated with Silane. Etching leaves a roughened surface on the porcelain, the Silane provides a chemical tag to which the composite bonding cement can bind. In general, if a laboratory fabricates the restoration, these steps are completed at the lab. Anytime a porcelain restoration returned from the lab needs to be adjusted in the dentist's office for a nonconforming fit, the newly exposed areas of porcelain must be re-etched with the acid gel and thereafter rinsed.

Currently, only one CAD/CAM system is available for dental office use. This system, manufactured by Sirona, is called Cerec. Using a Cerec the dentist is able to prepare the tooth, manufacture a porcelain dental restoration and cement it into the patient's mouth all in one visit. With this system the etching and silanation are always done in the dental office.

A prior technique to etch the milled restoration involved placing the crown on a gauze pad and applying the etching gel and rinsing. This technique proved to be awkward and prone to undesired over-spraying from the precise work area. Suctioning off of the liquid has the potential of losing the restoration into the suction line.

The present inventor has recognized the need for an easily usable, handheld etching and rinsing device useful for applying etching acid gel to a restoration and thereafter rinsing the restoration.

SUMMARY OF THE INVENTION

The present invention provides a useful device for treating and rinsing articles. The device includes a base component having a fluid drain, a tray or platform component for supporting an article to be treated and rinsed, and a shield component for containing over-spray during rinsing. The tray component includes one or more drain holes, or can be foraminous or otherwise perforated for rapid draining.

The tray component can be a separate component which is snap-fit to the base component and/or to the shield component, or can be formed with, or attached to, or held within the base component or the shield component.

The shield component is preferably cylindrical or frustoconical, tapered upwardly. The shield component allows a stream of rinsing agent, such as water, to be directed downwardly against the article held on the tray without causing splashing or over-spray outside of the device. Particularly, in the frustoconical embodiment, the angled wall redirects downwardly spray which is deflected upwardly off the tray or article. Additionally, the generally small top opening of the frustoconical shield component helps to set up a venturi effect at the small top opening. This tends to draw air into the shield component through the small top opening, which provides a further impediment to over spray exiting the shield component out of the small top opening.

The device is particularly useful for treating and rinsing acid etched dental restorations. In that regard, a method is set forth which is particularly effective. In the dental office, the patient's tooth is modeled or mapped by infrared light and then a porcelain restoration is milled from a block of porcelain using the model or map, particularly by using a CAD/CAM driven milling machine. After the restoration is milled the practitioner then places it on the tray component within the shield component. The base component is connected to a draining source, preferably a source of drainage suction. The practitioner then applies the etching gel to the crown within the shield component. After a preselected time period, the practitioner then directs a water stream into the shield and against the restoration to rinse the acid etching material off of the restoration. The restoration can be lightly jostled or moved with an instrument to allow complete treatment and rinsing of all surfaces of the restoration within the shield.

In addition to the above-recited method useful in dentistry, the device of the present invention could be useful for any method that incorporated a treating and/or rinsing of a small article in a confined environment to prevent over spray and spillage.

Numerous other advantages and features of the present invention will become readily apparent from the following detailed description of the invention and the embodiments thereof, from the claims and from the accompanying drawings.

Detailed DESCRIPTION OF THE PREFERRED EMBODIMENTS

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

Figure 1:
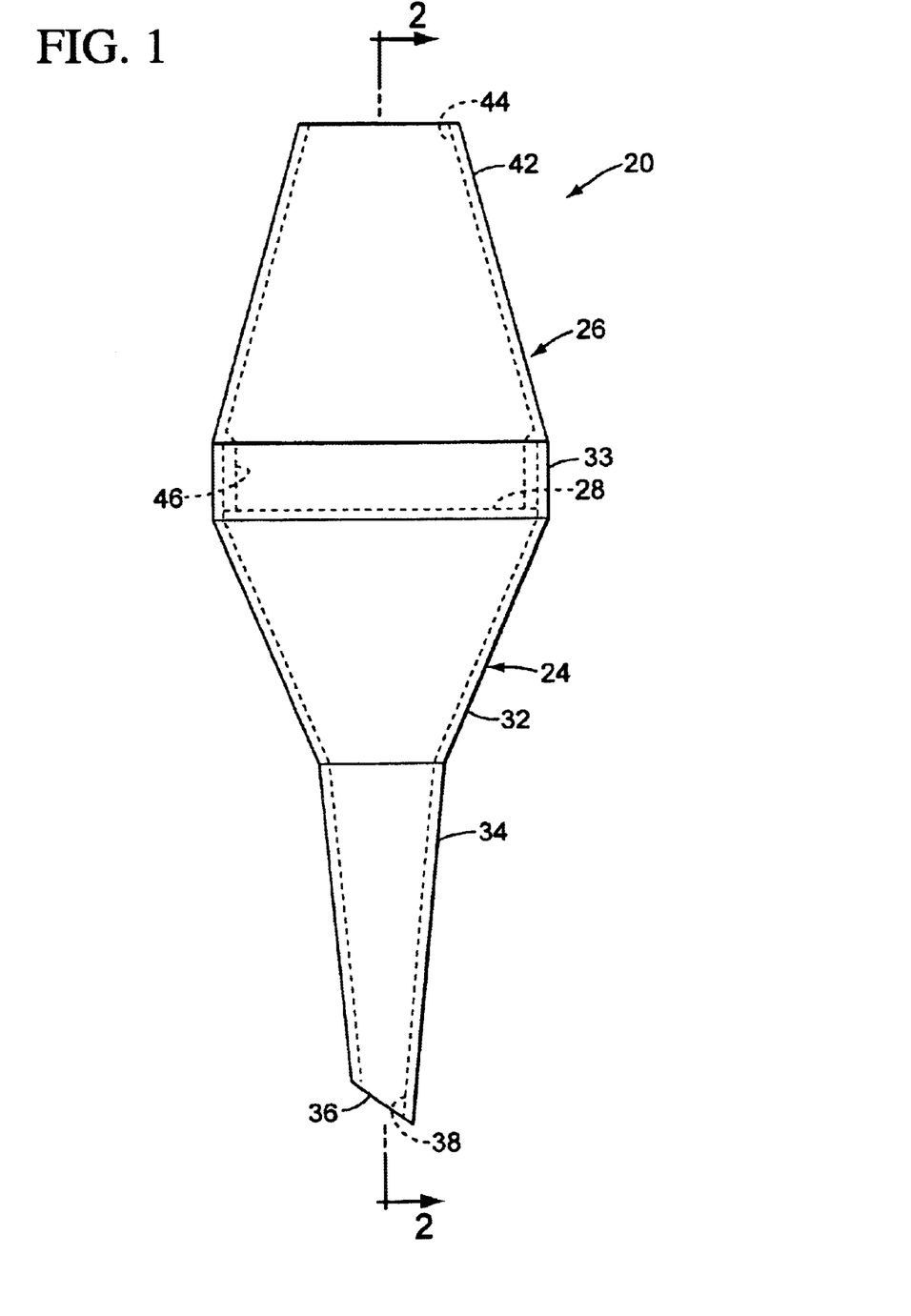
FIG. 1 is an elevation view of a first embodiment treating and rinsing device of the present invention.
Figure 2:
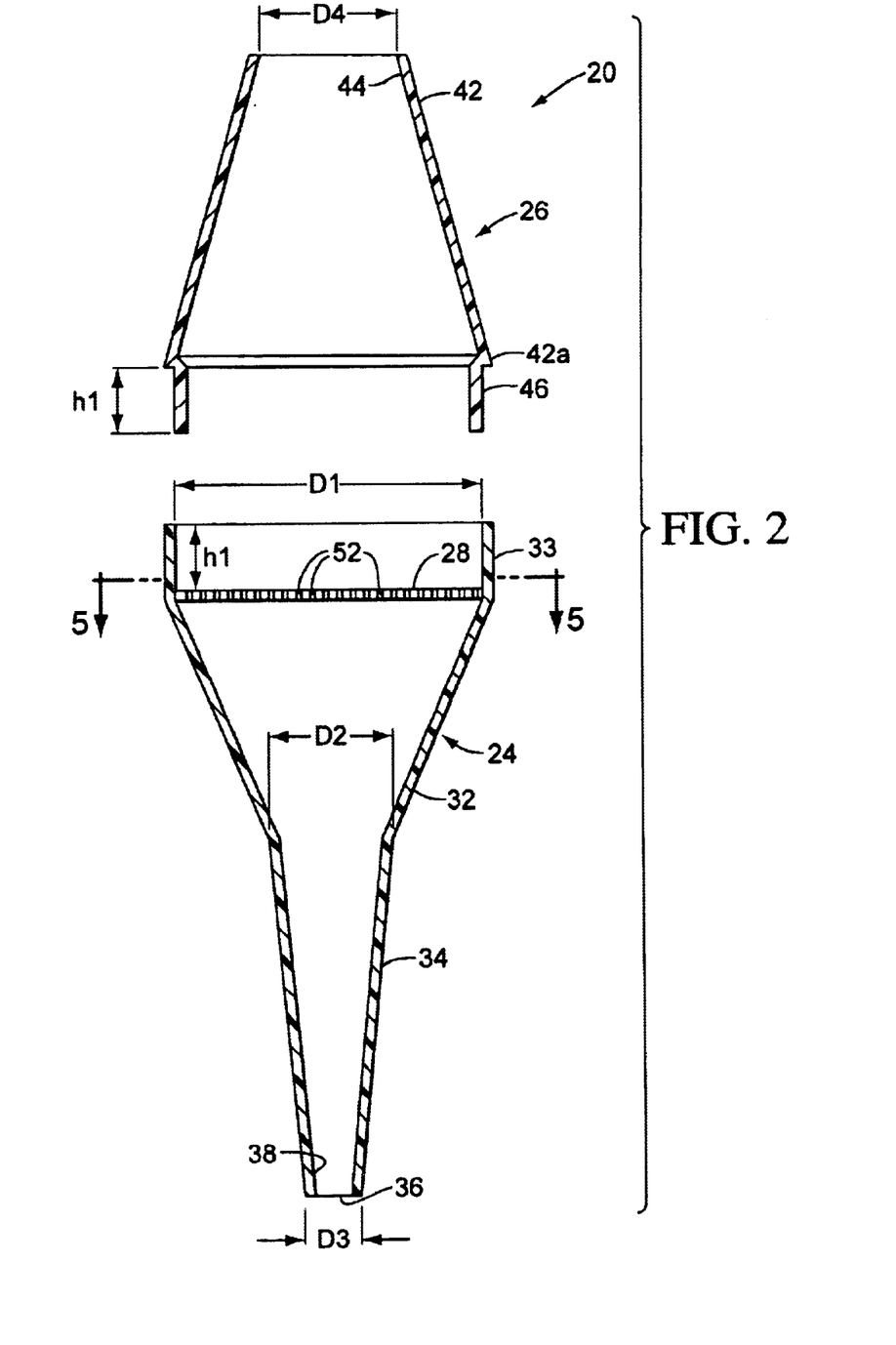
FIG. 2 is a sectional view taken generally along line 2—2 of FIG. 1.

FIG. 1 illustrates a treating and rinsing device 20, including a base component 24 and a shield component 26. A tray or platform component 28 is held within the base component 24 (as shown in FIG. 2). The base component 24 includes frustoconical manifold section 32 extended upwardly by a cylindrical section 33, and extended downwardly by a tapering tube section 34. The tube section 34 includes an angled end face 36. The end face 36 defines a drain opening 38.

The shield component 26 comprises a frustoconical body 42 having an open top end 44 and a base ring 46. The base ring 46 has an outside diameter sized to be tightly frictionally fit or snap fit into an inside diameter of the cylindrical section 33 of the base component 24. Alternatively, the base ring 46 and the cylindrical section 33 can be fastened together such as by being screwed together with an associated thread formation, or by means of a rib or ribs, and/or groove or grooves, or by any other known means of fastening cylindrical components.

Preferably, the base ring 46 has a height h1 equal to a depth of the cylindrical section 33 down to the platform component 28. The base ring 46 can thus serve to vertically retain the platform component 28. Also, by extending the ring 46 down to the platform component 28, no exposed bottom surface of the ring 46 is present to undesirably collect, and shelter from spray rinsing, acid gel thereon. This dimensioning of the ring 46 can be used for all the disclosed embodiments herein.

The platform component 28 is located within the cylindrical section 33. The platform component can be press fit in place or can be adhesively secured in place, or molded in place, or held in place by a groove or a rib within the base component. It is possible that the platform component is merely placed in its position and captured loosely within the base component.

The platform component comprises a plurality of holes or gaps 52 for drainage of liquid from above the platform component to below the platform component. The holes are preferably smaller than the smallest expected size of an article to be rinsed within the device. For treating and rinsing dental crowns, a maximum hole size of about 1.5 mm is preferred. A lower end 42a of the frustoconical body 42 has an outside diameter equal to an outside diameter of the cylindrical section 33 so that the shield component 26 and the base component 24, when engaged together, form a smooth transitionless, aesthetically pleasing form.

The preferred dimensions for the device 20 are as follows: an inside diameter D1 of cylindrical section 33 is equal to about 20–25 mm; and outside diameter D2 of a top of tubular section 34 is equal to about 12 mm; an outside diameter D3 of end face 36 is equal to about 8 mm; and an inside diameter D4 of top opening 44 is equal to about 10–15 mm. The outside diameter of the platform compared 28 is correspondingly about 20–25 mm. The above recited dimensions are exemplary only, and the invention is not limited to any particular dimensions.

The base component, shield component and platform component are preferably composed of plastic, sufficiently resistant to the acid used for etching and capable of being sterilized by steam autoclave.

Figure 3:
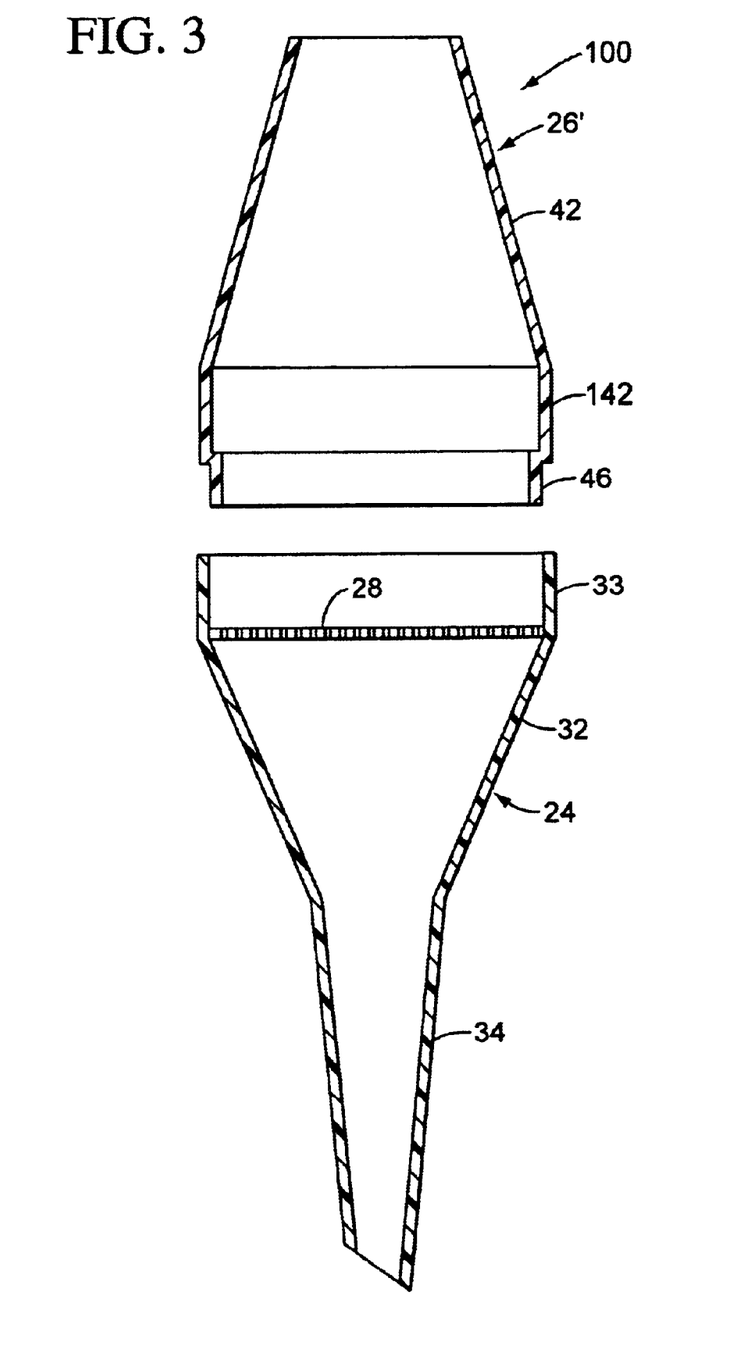
FIG. 3 is a sectional, exploded view of a second embodiment treating and rinsing device of the present invention.

FIG. 3 illustrates a second embodiment treating and rinsing device 100. In this embodiment the base component 24 is substantially the same as that described in the embodiment illustrated in FIGS. 1 and 2. An alternate shield 26' includes a bottom cylindrical section 142 having an outside diameter equal to an outside diameter of the cylindrical section 33 of the Base component. When the ring 46 is fit tightly within the cylindrical section 33, the cylindrical section 142 smoothly and transitionlessly continues to the cylindrical section 33. The embodiment of FIG. 3 provides an increased inside volume adjacent to the platform 28.

Figure 4:
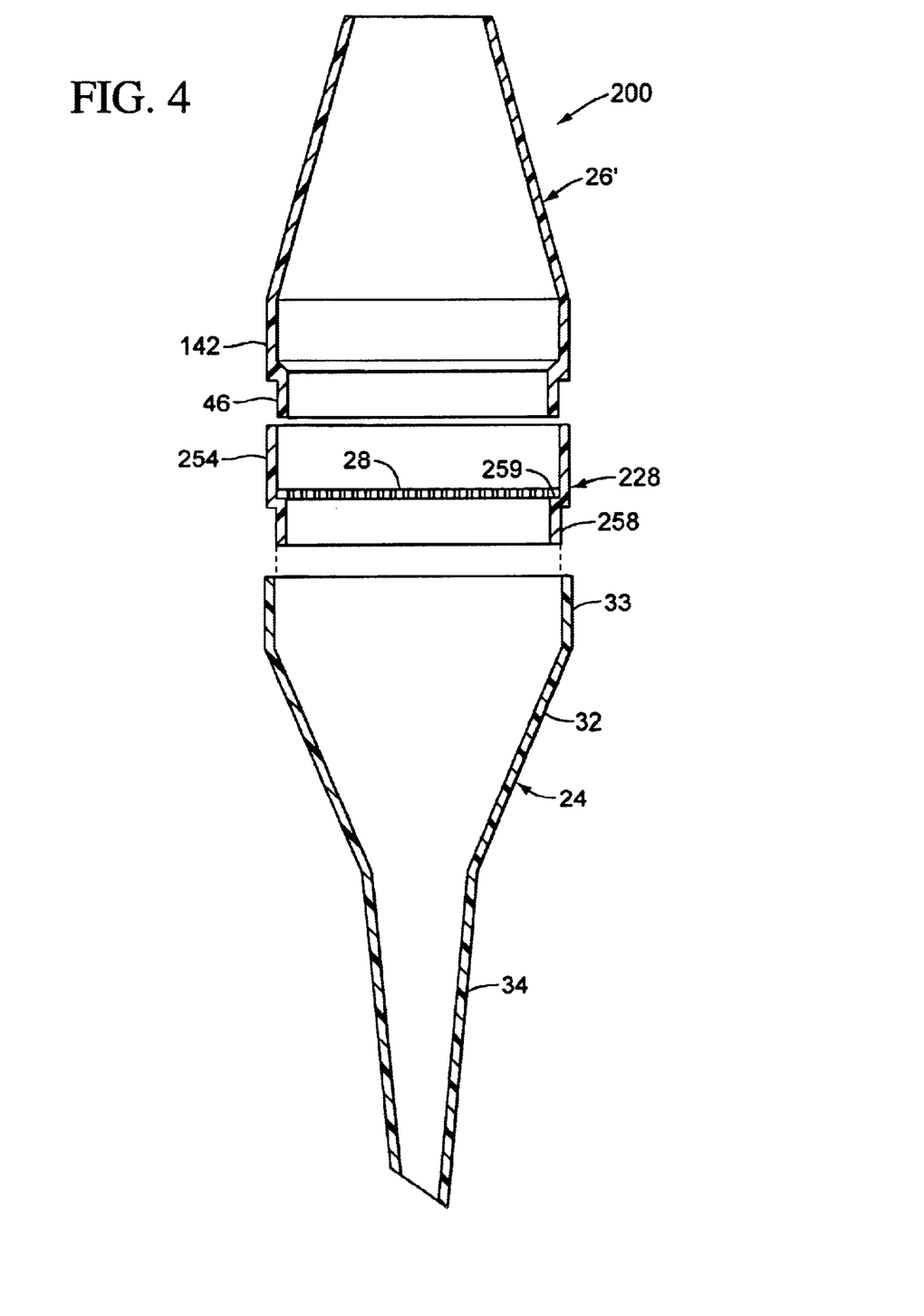
FIG. 4 is a sectional, exploded view of a third embodiment treatment and rinsing device of the present invention.

FIG. 4 illustrates a third embodiment treating and rinsing device 200. This device is a three part device including a base component 224, a shield component 26' and an intermediate platform-holding component 228.

The base component 224 is substantially identical to the base component 24 described above, except that the platform is absent from the base component.

The shield component 26' is substantially identical to that shown in FIG. 3. The ring 46 is sized to fit tightly into the intermediate component 228.

The intermediate component 228 includes a cylindrical section 254 having an inside diameter sized to tightly snap-fit engage the outside diameter of the ring 46. The outside diameter of the cylindrical section 254 matches the outside diameter of the cylindrical section 142. The intermediate component includes a snap ring 258 having an outside diameter sized to snap-fit into an inside diameter of the cylindrical section 33 of the base component. The outside diameter of the cylindrical section 254 of the intermediate section is equal to the outside diameter of the cylindrical section 33 of the base component.

The platform component 28 is placed on, or held on by means previously described, a ledge 259 formed within the intermediate component 228, above the snap ring 258.

Figure 4A:
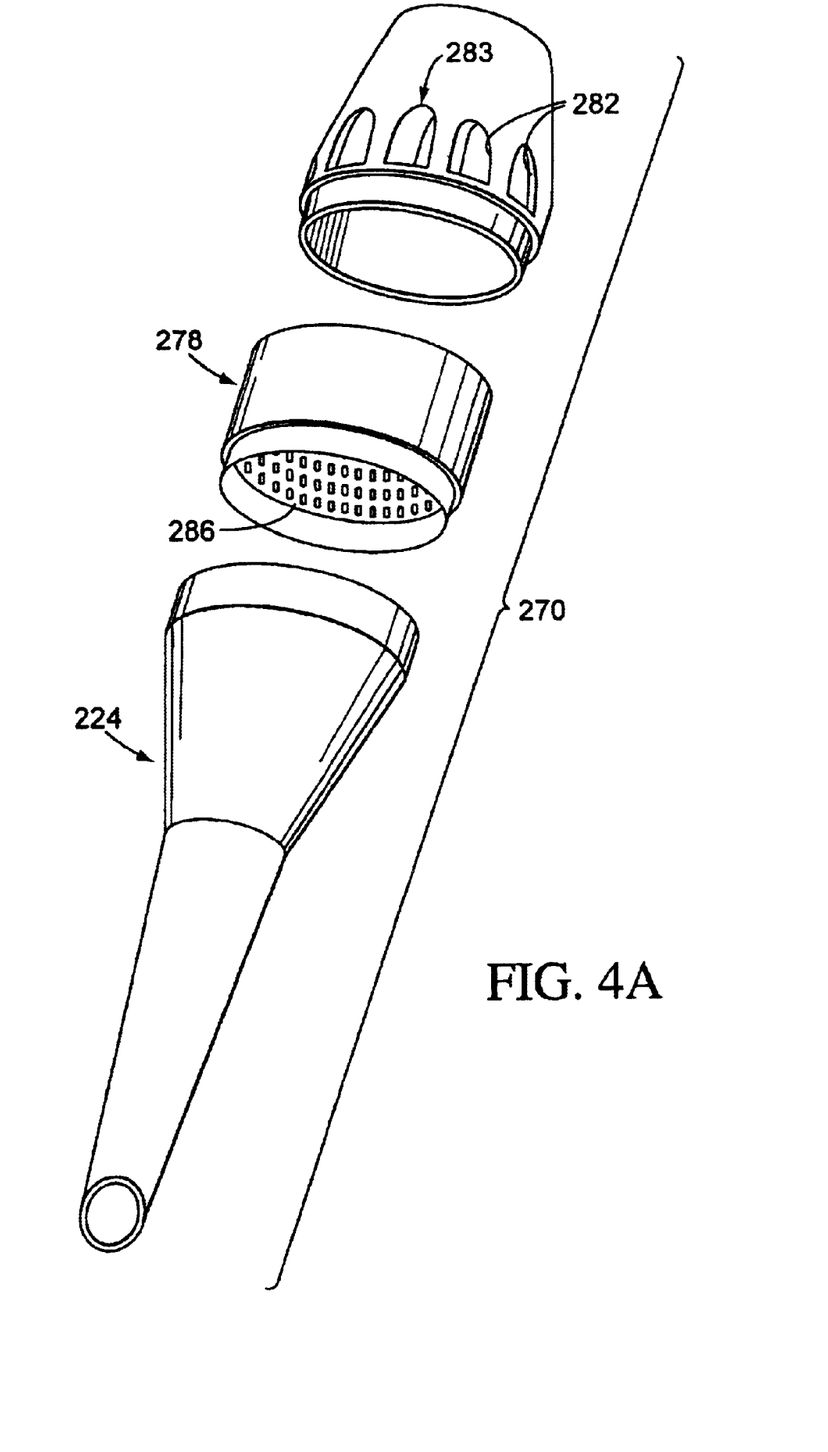
FIG. 4A is an exploded perspective view of a fourth embodiment treatment and rinsing device of the present invention.

FIG. 4A illustrates a fourth embodiment treating and rinsing device 270 having a shield component 274, an intermediate component 278 and the base component 224, previously described. The shield component 274 includes indentations 282 around a circumference thereof which provide a gripping surface 283. The gripping surface can be used to tightly assemble and thereafter disassemble the shield component 274 from the intermediate component 278. The intermediate component 278 and the base component 224 could also have gripping surfaces formed thereon to assist in assembly and disassembly.

The intermediate component 278 can carry a screen element 286. The screen element 286 can advantageously be molded with the component 278. The surface 286 shown has rectangular apertures.

In all other respects the device 270 assembles in a like manner as the device shown in FIG. 4.

The gripping surface 283 can also be used in any of the other embodiments. The integrally molded screen element 286 can be used in any of the other embodiments. Non-integrally molded screens can alternately be used in the intermediate component 278 as well.

Figure 5:
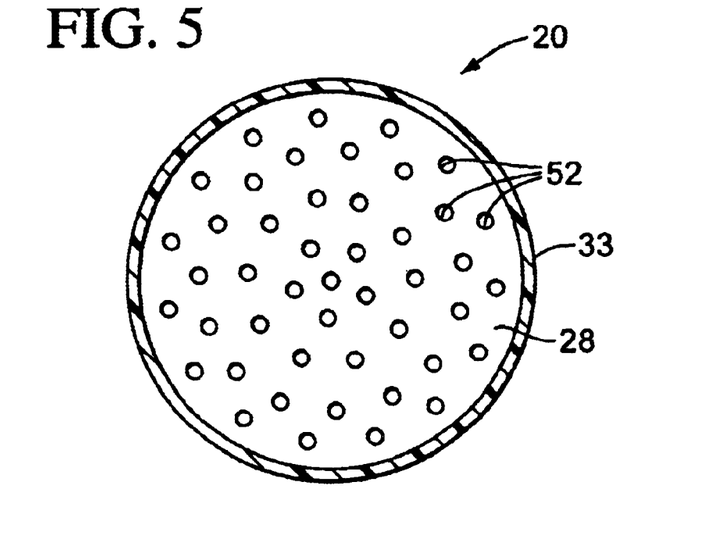
FIG. 5 is a plan view of a platform useable in the embodiments of FIGS. 1–4.

FIG. 5 illustrates the platform component 28, having perforations, openings, or holes 52 substantially over its entire surface. In this way a quick and complete draining through the platform component is insured.

Figure 6:
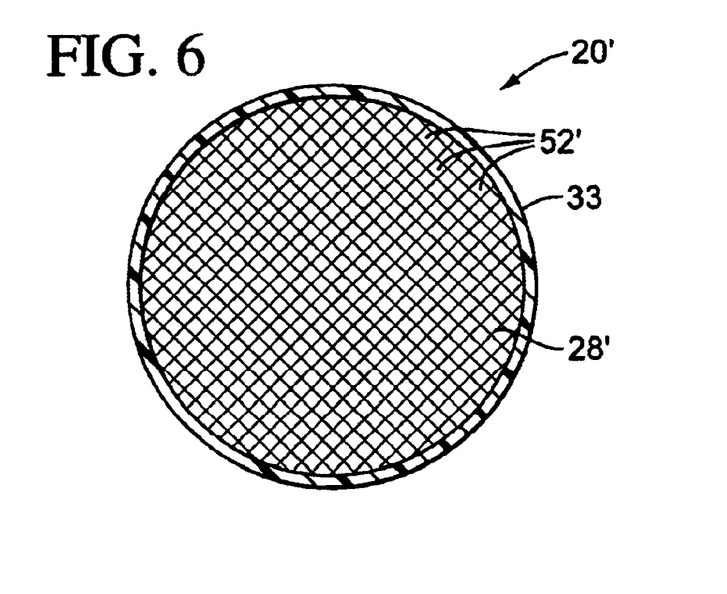
FIG. 6 is a plan view of an alternate platform useable in any of the embodiments of FIGS. 1–4.

FIG. 6 illustrates an alternate embodiment platform component 28' comprising a screen surface having regularly arranged gaps, spaces, or openings 52'.

Figure 7:
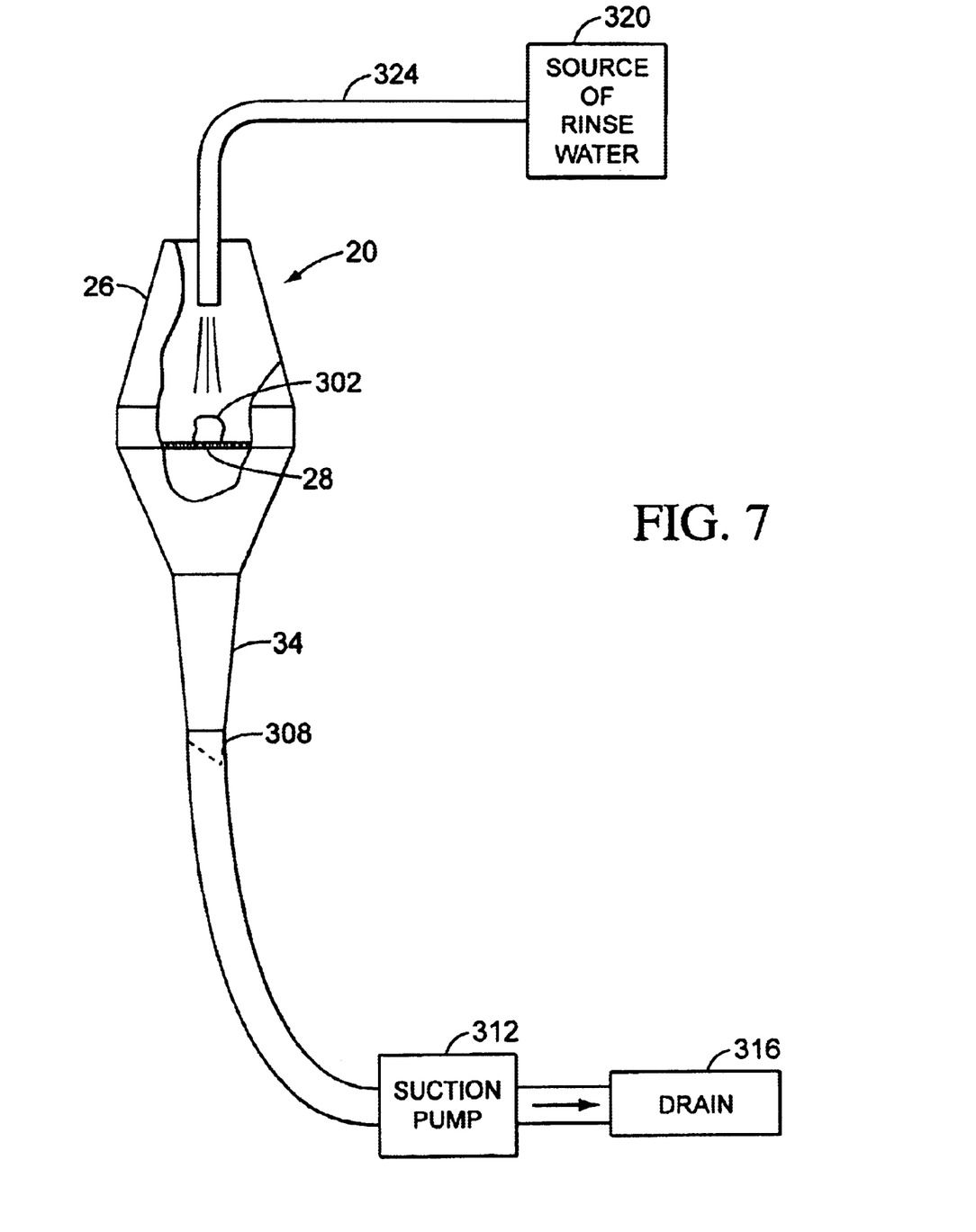
FIG. 7 is a diagrammatic block diagram of a method using the implement of FIG. 1.

FIG. 7 illustrates, in diagrammatic block form, the method of the invention. A portion of the device 20 is cut away for purposes of description. A restoration 302 is placed on the platform 28. The dental practitioner applies etching gel to the restoration. After a predetermined amount of time, the dental practitioner undertakes to rinse the etching gel off of the restoration. A suction tube 308 is placed over the end face 36 of the tube section 34. A suction pump 312 takes suction on the device 20 through the tube 308. The pump delivers liquid into a drain 316. A source of rinse water 320 delivers water at a relatively high velocity through a tube 324, held by the dental practitioner, and placed within the shield component 26 to spray water on the crown 302. The angled walls of the shield 26 prohibit deflecting spray from emerging from the relatively narrow top opening 44 during rinsing.

The invention encompasses a vessel having a base component, a shield component and a perforated platform component wherein the base component includes a drain hole and the shield component includes a top opening. The shield component, the base component and the platform component are connected together in fluid communication from the top opening through the drain hole.

The invention encompasses a method of etching and rinsing a restoration, wherein the restoration is placed on the aforementioned platform component within the shield component, etching acid is applied to the restoration and then the restoration is rinsed by spraying water through the top opening of the shield onto the restoration, and taking suction on the drain hole of the base component.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. An apparatus for treating a dental restoration with fluid, comprising:
 a base component having a first open top end and a bottom opening;
 a shield component mounted over said first open top end of said base component, said shield component having a second open top end and an open bottom end, said base component and said shield component defining a volume; and
 a perforated platform mounted within said volume, said second open top end being sufficiently large to allow a practitioner to apply a treatment to the dental restoration through the second open top end and to then rinse the dental restoration through the second open top end.

2. The apparatus according to claim 1, wherein said second open top end of said shield component is smaller than said open bottom end of said shield component.

3. The apparatus according to claim 1, wherein said base component comprises a tubular extension that terminates at said bottom opening.

4. The apparatus according to claim 1, wherein said platform is held within said volume by fixing of said shield component to said base component.

5. The apparatus according to claim 1, wherein said second open top end of said shield component is smaller than said open bottom end of said shield component; and wherein said base component comprises a tubular extension that terminates at said bottom opening.

6. The apparatus according to claim 1, said perforated platform comprises a screen.

7. The apparatus according to claim 1, wherein said base component is tapered along at least half of the longitudinal distance between said first open top end and said bottom opening; and
 wherein said shield component is tapered along at least half of the longitudinal distance between said open bottom end and said second open top end.

8. An apparatus for treating a dental restoration with fluid, comprising:
 a base component having an open top end and a bottom opening;
 a shield component mounted over said open top end of said base component, said shield component having a top opening and an open bottom end, said base component and said shield component defining a volume; and
 a perforated platform mounted within said volume;
 wherein said platform is held within said volume by fixing of said shield component to said base component.

9. A vessel for holding a dental restoration for treating with a fluid, comprising:
 a tube;
 a means for drawing suction through said tube;
 a shell having an open top end and a fluid exit opening configured to be flow connected to said tube;
 a platform carried within the shell, said platform arranged to support a restoration, said platform providing at least one opening for passing fluid from said open top end to said exit opening, said open top end being sufficiently large to allow a practitioner to apply a treatment to the dental restoration through the open top end and to then rinse the dental restoration through the open top end.

10. The vessel according to claim 9, wherein said shell comprises a tubular portion and said fluid exit opening is located at an end of said tubular portion.

11. The vessel according to claim 9, wherein said shell comprises a tubular part extending upwardly of said platform, said open top end located at an end of said tubular part.

12. The vessel according to claim 11, wherein said tubular part is tapered in a direction away from said platform.

13. The vessel according to claim 9, wherein said platform comprises a perforated plate.

14. The vessel according to claim 9, wherein said platform comprises a screen.

15. The vessel according to claim 9, wherein said shell comprises a surface treatment forming a gripping surface.

16. The vessel according to claim 9, wherein said shell is separable at an intermediate position thereof to remove or install said platform.

17. The vessel according to claim 9, wherein said shell comprises a shield portion defining said open top end, a ring-shaped piece, and a base portion defining said fluid exit opening, and said ring-shaped piece being fixed between said shield portion and said base portion, said platform carried by said ring-shaped piece, said shield portion, said ring-shaped piece, and said base portion having corresponding central passages in fluid communication.

18. The apparatus according to claim 17, wherein said shield portion is tapered along at least half of the longitudinal distance between said ring-shaped piece and said open top end; and wherein said base portion is tapered along at least half of the longitudinal distance between said ring-shaped piece and said fluid exit opening.

19. The apparatus according to claim 19, wherein said shell is tapered along at least half of the longitudinal distance between said platform and said open top end; and wherein said shell is tapered along at least half of the longitudinal distance between said platform and said fluid exit opening.

20. A vessel for holding a dental restoration for treating with a fluid, comprising:

a shell having a fluid inlet opening and a fluid exit opening;

a platform carried within the shell, said platform arranged to support a restoration, said platform providing at least one opening for passing fluid from said inlet opening to said exit opening;

wherein said shell is separable at a intermediate position thereof to remove or install said platform.

21. A vessel for holding a dental restoration for treating with a fluid, comprising:

a shell having a fluid inlet opening and a fluid exit opening;

a platform carried within the shell, said platform arranged to support a restoration, said platform providing at least one opening for passing fluid from said inlet opening to said exit opening;

wherein said shell comprises a shield portion, a ring-shaped piece, and a base portion, and said ring-shaped piece being fixed between said shield portion and said base portion, said platform carried by said ring-shaped piece, said shield portion, said ring-shaped piece, and said base portion having corresponding central passages in fluid communication.

22. The vessel according to claim 21, wherein said shield portion is tapered in a direction extending away from said ring-shaped piece, and said base portion is tapered in a direction extending away from ring-shaped piece.

23. A method of treating a dental restoration with a fluid, comprising the steps of:

providing a shell having a fluid opening and an outlet opening, and a perforated platform located between the inlet opening and the outlet opening;

placing a dental restoration on said platform within said shell;

injecting fluid through said inlet opening onto said dental restoration;

removing said fluid out of said outlet opening.

24. The method according to claim 23, comprising the further step of drawing suction on said outlet opening.

25. The method according to claim 23, wherein said step of injecting fluid is further defined in that said fluid is sprayed directly onto said dental restoration.

26. The method according to claim 23, wherein said step of providing a shell is further defined in that said shell comprises a shield portion extending upwardly from said platform, said shield portion having a tapered profile extending upwardly from said platform and said inlet opening is smaller in width than said perforated platform.

27. The method according to claim 26, wherein said shield portion comprises a frustoconical shape.

28. The method according to claim 26, comprising the further step of applying a gel treatment onto said dental restoration while carried on said platform, said applying step before the step of injecting fluid, wherein said step of injecting fluid is further characterized as a rinsing step to rinse off the gel treatment.

29. The method according to claim 23, comprising the further step of applying a gel treatment onto said dental restoration while carried on said platform, said applying step before the step of injecting fluid, wherein said step of injecting fluid is further characterized as a rinsing step to rinse off the gel treatment.

30. The method according to claim 29, wherein said step of injecting fluid is further defined in that said fluid is sprayed directly onto said dental restoration, and wherein said step of removing said fluid is further defined in that suction is drawn on said outlet opening during said injecting fluid step.

* * * * *

UNITED STATES PATENT AND TRADEMARK OFFICE
CERTIFICATE OF CORRECTION

PATENT NO. : 6,811,398 B2
DATED : November 2, 2004
INVENTOR(S) : Donald L. Bennett It is certified that error appears in the above-identified patent and that said Letters Patent is hereby corrected as shown below:

Column 7,
Line 4, correct "19" to -- 9 --.

Signed and Sealed this

Sixteenth Day of August, 2005

JON W. DUDAS
*Director of the United States Patent and Trademark Office*